(12) United States Patent
Fujimoto et al.

(10) Patent No.: US 10,615,456 B2
(45) Date of Patent: Apr. 7, 2020

(54) ADDITIVE FOR NONAQUEOUS ELECTROLYTE SOLUTIONS, NONAQUEOUS ELECTROLYTE SOLUTION AND ELECTRICITY STORAGE DEVICE

(71) Applicant: Sumitomo Seika Chemicals Co., Ltd., Kako-gun, Hyogo (JP)

(72) Inventors: Shohei Fujimoto, Hyogo (JP); Yuki Kono, Hyogo (JP); Koji Fujita, Hyogo (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 26 days.

(21) Appl. No.: 15/772,709

(22) PCT Filed: Nov. 4, 2016

(86) PCT No.: PCT/JP2016/082832
§ 371 (c)(1),
(2) Date: May 1, 2018

(87) PCT Pub. No.: WO2017/078149
PCT Pub. Date: May 11, 2017

(65) Prior Publication Data
US 2019/0181499 A1 Jun. 13, 2019

(30) Foreign Application Priority Data
Nov. 6, 2015 (JP) .................. 2015-218718

(51) Int. Cl.
*H01M 10/00* (2006.01)
*H01M 10/0567* (2010.01)
(Continued)

(52) U.S. Cl.
CPC ....... *H01M 10/0567* (2013.01); *C07C 311/01* (2013.01); *C07C 311/09* (2013.01);
(Continued)

(58) Field of Classification Search
CPC ....... H01M 2300/0028; H01M 10/052; H01M 10/0567; H01M 10/0568; H01M 10/0569;
(Continued)

(56) References Cited

U.S. PATENT DOCUMENTS 6,063,522 A * 5/2000 Hamrock .............. H01M 6/183
429/200
2013/0337317 A1 12/2013 Shima et al.

FOREIGN PATENT DOCUMENTS

CN 1289765 4/2001
CN 103004006 3/2013
(Continued)

OTHER PUBLICATIONS

Chung, et al., "Origin of Graphite Exfoliation—An Investigation of the Important Role of Solvent Cointercalation", Journal of the Electrochemical Society, 147 (12), 4391-4398 (2000).
(Continued)

*Primary Examiner* — Cynthia H Kelly
*Assistant Examiner* — Monique M Wills
(74) *Attorney, Agent, or Firm* — Hamre, Schumann, Mueller & Larson, P.C.

(57) ABSTRACT

Disclosed is an additive for nonaqueous electrolyte solutions, comprising a disulfonic acid amide compound represented by Formula (1).

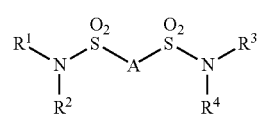

(1)

In Formula (1), A represents a $C_mH_{(2m-n)}Z_n$, in which m represents an integer of 1 to 6, n represents an integer of 1
(Continued)

to 12, 2m-n is 0 or more, and Z represents a halogen atom, $R^1$, $R^2$, $R^3$, and $R^4$ represent an alkyl group having 1 to 6 carbon atoms which is substituted with a phenyl group optionally having a substituent, or the like, and $R^1$ and $R^2$, and $R^3$ and $R^4$ may be linked respectively to form an alkylene group having 2 to 5 carbon atoms in total which forms a cyclic structure together with a nitrogen atom.

12 Claims, 1 Drawing Sheet

(51) Int. Cl.

| | | |
|---|---|---|
| *H01G 11/64* | (2013.01) | |
| *H01M 10/0568* | (2010.01) | |
| *H01M 10/0569* | (2010.01) | |
| *H01M 10/052* | (2010.01) | |
| *C07C 311/09* | (2006.01) | |
| *C07D 295/26* | (2006.01) | |
| *H01G 11/06* | (2013.01) | |
| *C07C 311/01* | (2006.01) | |
| *H01M 10/0525* | (2010.01) | |
| *H01G 11/60* | (2013.01) | |
| *H01G 11/62* | (2013.01) | |
| *H01G 11/50* | (2013.01) | |
| *H01M 4/62* | (2006.01) | |

(52) U.S. Cl.
CPC ........... *C07D 295/26* (2013.01); *H01G 11/06* (2013.01); *H01G 11/64* (2013.01); *H01M 10/052* (2013.01); *H01M 10/0525* (2013.01); *H01M 10/0568* (2013.01); *H01M 10/0569* (2013.01); *H01G 11/50* (2013.01); *H01G 11/60* (2013.01); *H01G 11/62* (2013.01); *H01M 4/623* (2013.01); *H01M 2300/0028* (2013.01); *Y02E 60/13* (2013.01)

(58) Field of Classification Search
CPC ........ H01G 11/06; H01G 11/60; H01G 11/62; C07C 311/09
See application file for complete search history.

(56) References Cited

FOREIGN PATENT DOCUMENTS

| | | |
|---|---|---|
| EP | 1 088 814 | 4/2001 |
| EP | 2731187 | 5/2014 |
| JP | 63-102173 | 5/1988 |
| JP | 5-074486 | 3/1993 |
| JP | 5-258753 | 10/1993 |
| JP | 11-339850 | 12/1999 |
| JP | 2000-003724 | 1/2000 |
| JP | 2001-052735 | 2/2001 |
| JP | 2004-281325 | 10/2004 |
| JP | 2005-203341 | 7/2005 |
| JP | 2005-228631 | 8/2005 |
| JP | 2006-227359 | 8/2006 |
| JP | 2009-038018 | 2/2009 |
| JP | 2014-013728 | 1/2014 |
| JP | 2014-013729 | 1/2014 |
| JP | 2014-194872 | 10/2014 |
| TW | 201304239 | 1/2013 |
| WO | 2012/170240 | 12/2012 |
| WO | 2013/005828 | 1/2013 |

OTHER PUBLICATIONS

English translation of the International Preliminary Report on Patentability (IPRP) issued in International Application No. PCT/JP2016/082832, issued May 8, 2018, dated May 17, 2018, 7 pages.
The extended European Search Report issued in counterpart EP Patent Application No. 16862208.2, dated Aug. 22, 2019, 5 pages.
Notice of Allowance issue in counterpart Taiwanese Patent Application No. 105135938, dated Feb. 12, 2020, 3 pages.

* cited by examiner

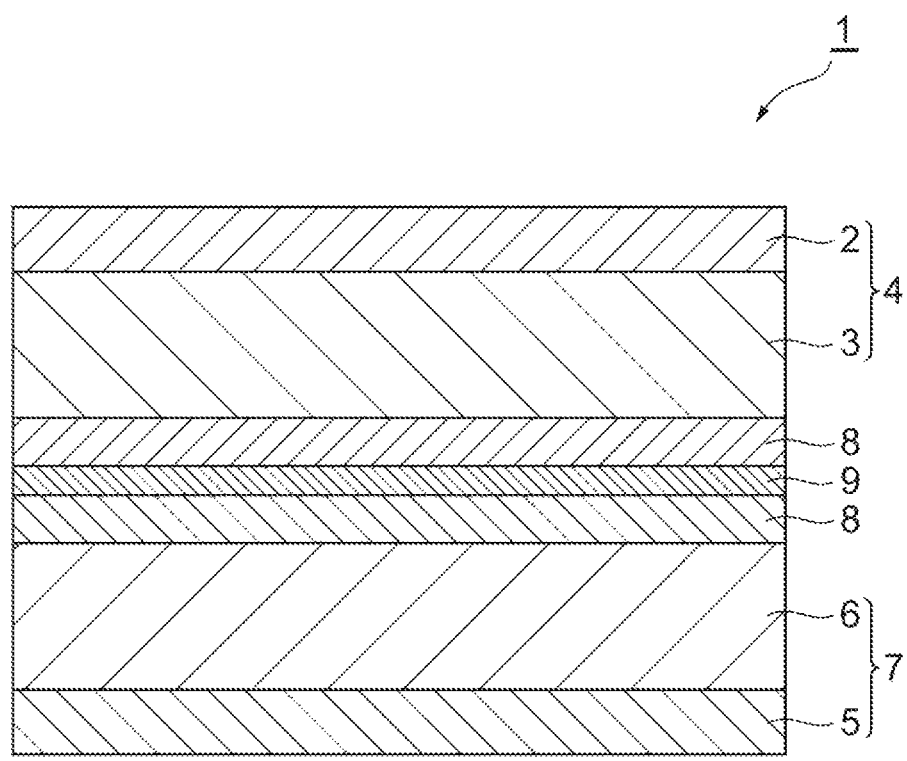

ADDITIVE FOR NONAQUEOUS ELECTROLYTE SOLUTIONS, NONAQUEOUS ELECTROLYTE SOLUTION AND ELECTRICITY STORAGE DEVICE

TECHNICAL FIELD

The present invention relates to an additive for nonaqueous electrolyte solutions. In addition, the invention relates to a nonaqueous electrolyte solution using the additive for nonaqueous electrolyte solutions, and an electricity storage device using the nonaqueous electrolyte solution.

BACKGROUND ART

In recent years, along with an increase in attention to solving environmental problems and establishing a sustainable recycling-based society, electricity storage devices such as nonaqueous electrolyte solution secondary batteries typified by lithium ion batteries, and electric double layer capacitors have been widely studied. Among these, the lithium ion batteries are used as power sources for laptops, mobile phones, and the like due to the fact that they have high working voltages and energy densities. Expectations are placed on these lithium ion batteries due to the fact that such lithium ion batteries have higher energy densities than lead batteries and nickel-cadmium batteries and allow realization of a higher capacity.

However, the lithium ion batteries have a problem in that the capacity of the batteries decreases over time in charge/discharge cycles.

As a method for suppressing a reduction in the capacity of batteries due to charge/discharge cycles, a method in which various additives are added to an electrolyte solution have been examined. The additives are decomposed during an initial stage of charge and discharge to form a film called a solid electrolyte interface (SEI) on the surface of an electrode. Since the SEI is formed during an initial cycle of charge/discharge cycles, electricity is not consumed for decomposition of a solvent or the like in the electrolyte solution, and lithium ions can be transferred between electrodes through the SEI. That is, the formation of an SEI is considered to prevent electricity storage devices such as nonaqueous electrolyte solution secondary batteries from being deteriorated during the repeating charge/discharge cycles, and make a great contribution to an improvement in battery characteristics, storage characteristics, load characteristics, or the like.

As an additive for an electrolyte solution that forms the SEI, for example, Patent Literatures 1 to 3 disclose cyclic monosulfonic acid esters. Patent Literature 4 discloses a sulfur-containing aromatic compound, and Patent Literature 5 discloses a disulfide compound. Patent Literatures 6 to 9 disclose disulfonic acid esters.

CITATION LIST

Patent Literature

[Patent Literature 1] Japanese Unexamined Patent Publication No. S63-102173
[Patent Literature 2] Japanese Unexamined Patent Publication No. 2000-003724
[Patent Literature 3] Japanese Unexamined Patent Publication No. H11-339850
[Patent Literature 4] Japanese Unexamined Patent Publication No. H05-258753
[Patent Literature 5] Japanese Unexamined Patent Publication No. 2001-052735
[Patent Literature 6] Japanese Unexamined Patent Publication No. 2009-038018
[Patent Literature 7] Japanese Unexamined Patent Publication No. 2005-203341
[Patent Literature 8] Japanese Unexamined Patent Publication No. 2004-281325
[Patent Literature 9] Japanese Unexamined Patent Publication No. 2005-228631
[Patent Literature 10] Japanese Unexamined Patent Publication No. H5-74486
[Patent Literature 11] Japanese Unexamined Patent Publication No. 2014-013728

SUMMARY OF INVENTION

Technical Problem

Regarding an adaptability indicator of an additive for nonaqueous electrolyte solutions with respect to electrochemical reduction in an electrode of nonaqueous electrolyte solution secondary batteries, a method of using an energy level of the lowest unoccupied molecular orbital (LUMO) energy of a compound constituting the additive for nonaqueous electrolyte solutions has been reported, for example, in "Geun-Chang, Hyung-Jin kim, Seung-ll Yu, Song-Hui Jun, Jong-Wook Choi, Myung-Hwan Kim. Journal of The Electrochemical Society, 147, 12, 4391 (2000)". According to this literature, a compound with lower LUMO energy is an excellent electron acceptor and becomes an additive for nonaqueous electrolyte solutions that can form a stable SEI on the surface of an electrode of nonaqueous electrolyte solution secondary batteries or the like. Accordingly, this method, which can easily evaluate whether a compound has a capability of forming a stable SEI on the surface of an electrode of electricity storage devices such as nonaqueous electrolyte solution secondary batteries by measuring a LUMO energy of the compound, is now a very useful tool.

On the other hand, compounds disclosed in Patent Literatures 1 to 9 are problematic in that the compounds have a high LUMO energy and does not necessarily have a capability as an additive for nonaqueous electrolyte solutions, or have low LUMO energy but lack chemical stability. In particular, disulfonic acid esters exhibit low LUMO energy. However, such esters have a low stability against moisture and are easily deteriorated. Thus, in a case of storage thereof, strict control of water content and temperature is required.

An electrolyte solution in which the vinylene carbonate-based compound described in Patent Literature 10 is used as an additive for nonaqueous electrolyte solutions had a problem such as generation of gas including carbon dioxide during the decomposition of vinylene carbonate on the electrode, which leads to a reduction in battery performance. Generation of the gas is noticeable, particularly in the repeating charge/discharge cycles at a high temperature or in a long period of time.

A disulfonic acid amide compound described in Patent Literature 11 is highly stable and brings about relatively good effects in battery characteristics such as maintenance of discharge capacity and internal resistance ratio. However, the compound is not sufficient with respect to an effect of suppressing gas generation.

As described above, sufficient performance cannot be obtained from an additive for nonaqueous electrolyte solutions in the related art, and development of a novel additive for nonaqueous electrolyte solutions that improves battery characteristics of an electricity storage device has been required.

Accordingly, an object of the invention is to provide an additive for nonaqueous electrolyte solutions that has excellent storage stability and can form a stable SEI so that cycle characteristics are improved and gas generation is also suppressed, in a case of being used in an electricity storage device such as a nonaqueous electrolyte solution secondary battery. Another object of the invention is to provide a nonaqueous electrolyte solution using the additive for nonaqueous electrolyte solutions and an electricity storage device using the nonaqueous electrolyte solution.

Solution to Problem

One aspect of the invention provide an additive for nonaqueous electrolyte solutions, comprising a disulfonic acid amide compound represented by Formula (1).

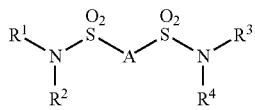

In Formula (1), A represents a $C_mH_{(2m-n)}Z_n$, in which m represents an integer of 1 to 6, n represents an integer of 1 to 12, 2m-n is 0 or more, and Z represents a halogen atom.

$R^1$ represents a phenyl group optionally having a substituent, a phenylthio group optionally having a substituent, a phenoxy group optionally having a substituent, a phenylamino group optionally having a substituent, or an alkyl group having 1 to 6 carbon atoms which is substituted with a phenyl group optionally having a substituent, in which a sulfur atom, an oxygen atom, or an amino group optionally having a substituent may intervene between two carbon atoms of the alkyl group, between one carbon atom of the alkyl group and the phenyl group optionally having a substituent, or between one carbon atom of the alkyl group and a nitrogen atom to which $R^1$ is bonded. In other words, $R^1$ represents a phenyl group optionally having a substituent or an alkyl group having 1 to 6 carbon atoms which has a phenyl group in its carbon chain or at its side chain and may have a sulfur atom, an oxygen atom, or a nitrogen atom in its carbon chain or at its side chain.

$R^2$, $R^3$, and $R^4$ each independently represent a hydrogen atom, a phenyl group optionally having a substituent, a phenylthio group optionally having a substituent, a phenoxy group optionally having a substituent, a phenylamino group optionally having a substituent, or an alkyl group having 1 to 6 carbon atoms which may be substituted with a phenyl group optionally having a substituent, in which a sulfur atom, an oxygen atom, or an amino group optionally having a substituent may intervene between two carbon atoms of the alkyl group, between one carbon atom of the alkyl group and the phenyl group optionally having a substituent, or between one carbon atom of the alkyl group and a nitrogen atom to which $R^2$, $R^3$, or $R^4$ is bonded. In other words, $R^2$, $R^3$, and R each independently represent a hydrogen atom, a phenyl group optionally having a substituent, or an alkyl group having 1 to 6 carbon atoms which may have a sulfur atom, an oxygen atom, a nitrogen atom, or a phenyl group in its carbon chain or at its side chain.

$R^1$ and $R^2$ may be linked to form an alkylene group having 2 to 5 carbon atoms in total which forms a cyclic structure together with a nitrogen atom to which they are bonded, in which a sulfur atom, an oxygen atom, or an amino group optionally having a substituent may intervene between two carbon atoms of the alkylene group, or between one carbon atom of the alkylene group and the nitrogen atom to which $R^1$ and $R^2$ are bonded. In other words, $R^1$ and $R^2$ may be linked to form a cyclic structure together with a nitrogen atom to which they are bonded, in which case $R^1$ and $R^2$ are an alkylene group having 2 to 5 carbon atoms in total which may have a sulfur atom, an oxygen atom, or a nitrogen atom in its carbon chain or at its carbon chain end.

$R^3$ and $R^4$ may be linked to form an alkylene group having 2 to 5 carbon atoms in total which forms a cyclic structure together with a nitrogen atom to which they are bonded, in which a sulfur atom, an oxygen atom, or an amino group optionally having a substituent may intervene between two carbon atoms of the alkylene group, or between one carbon atom of the alkylene group and the nitrogen atom to which $R^3$ and $R^4$ are bonded. In other words, $R^3$ and $R^4$ may be linked to form a cyclic structure together with a nitrogen atom to which they are bonded, in which case $R^3$ and $R^4$ are an alkylene group having 2 to 5 carbon atoms in total which may have a sulfur atom, an oxygen atom, or a nitrogen atom in its carbon chain or at its side chain.

Advantageous Effects of Invention

According to one aspect of the invention, it is possible to provide an additive for nonaqueous electrolyte solutions which has excellent storage stability and can form a stable SEI on the surface of an electrode so that cycle characteristics are improved in charge/discharge capacity, internal resistance, and the like, and gas generation is also suppressed, in a case of being used in an electricity storage device such as a nonaqueous electrolyte solution secondary battery. According to another aspect of the invention, it is possible to provide a nonaqueous electrolyte solution using the additive for nonaqueous electrolyte solutions and an electricity storage device using the nonaqueous electrolyte solution.

BRIEF DESCRIPTION OF DRAWINGS

FIG. 1 is a cross-sectional view schematically showing an embodiment of a nonaqueous electrolyte solution secondary battery as an example of an electricity storage device.

DESCRIPTION OF EMBODIMENTS

Hereinafter, embodiments of the invention will be described in detail. However, the invention is not limited to the following embodiment.

An additive for nonaqueous electrolyte solutions according to an embodiment includes a disulfonic acid amide compound represented by Formula (1).

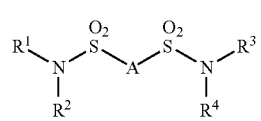

In Formula (1), A represents a $C_mH_{(2m-n)}Z_n$, in which m represents an integer of 1 to 6, n represents an integer of 1 to 12, 2m-n is 0 or more, and Z represents a halogen atom.

The present inventors have found that the disulfonic acid amide compound represented by Formula (1) exhibits low LUMO energy, which makes susceptible to electrochemical reduction, and is chemically stable. The present inventors have further found that in a case where an additive for nonaqueous electrolyte solutions containing the disulfonic acid amide compound is used in a nonaqueous electrolyte solution and the nonaqueous electrolyte solution is used in an electricity storage device such as a nonaqueous electrolyte solution secondary battery, the disulfonic acid amide compound is decomposed during an initial stage of charge and discharge to form a stable SEI on the surface of an electrode so that not only cycle characteristics are improved but also gas generation is suppressed.

The reason why the additive for nonaqueous electrolyte solutions containing the disulfonic acid amide compound represented by Formula (1) not only improves the cycle characteristics but also suppresses the gas generation is not completely found, but it is thought as follows. It is considered that the disulfonic acid amide compound represented by Formula (1) forms an SEI containing a large number of polar groups including N, S, O, a halogen atom, and the like in a case of being subjected to electrochemical reduction. It is considered that such SEI containing a large number of polar groups including N, S, O, a halogen atom, and the like can exhibit excellent ionic conductivity, and can suppress the gas generation particularly by an effect of the halogen atom.

The group "$C_mH_{(2m-n)}Z_n$" as A in Formula (1) has a structure in which m carbon atoms are linked in a straight chain or a branched chain, and carbon atoms at both ends thereof are bonded to a sulfone group. Each of n halogen atoms Z is bonded to any one of m carbon atoms. A preferable upper limit of m is 4 and a more preferable upper limit thereof is 2, and a preferable lower limit of m is 1. A is preferably a methylene group or ethylene group having two or more halogen atoms.

Examples of the halogen atom represented by Z include a fluorine atom, a chlorine atom, and an iodine atom. Among these, from the viewpoint of exhibiting a lower LUMO value, a fluorine atom is preferable.

In Formula (1), $R^1$ represents a phenyl group optionally having a substituent, a phenylthio group optionally having a substituent, a phenoxy group optionally having a substituent, a phenylamino group optionally having a substituent, or an alkyl group having 1 to 6 carbon atoms which is substituted with a phenyl group optionally having a substituent.

In Formula (1), $R^2$, $R^3$, and $R^4$ each independently represent a hydrogen atom, a phenyl group optionally having a substituent, a phenylthio group optionally having a substituent, a phenoxy group optionally having a substituent, a phenylamino group optionally having a substituent, or an alkyl group having 1 to 6 carbon atoms which may be substituted with a phenyl group optionally having a substituent.

In the "alkyl group having 1 to 6 carbon atoms which is substituted with a phenyl group optionally having a substituent" or "alkyl group having 1 to 6 carbon atoms which may be substituted with a phenyl group optionally having a substituent" as $R^1$, $R^2$, $R^3$, or $R^4$ in Formula (1), a sulfur atom, an oxygen atom, or an amino group optionally having a substituent may intervene between two carbon atoms thereof, between one carbon atom thereof and the phenyl group optionally having a substituent, or between one carbon atom thereof and a nitrogen atom to which $R^1$ is bonded. Here, the intervention of a sulfur atom or the like between the two carbon atoms means that the two carbon atoms are connected via a sulfur atom (—S—) or the like which is covalently bonded to each of the carbon atoms. For example, the sulfur atom contained in "—CH$_2$—S—CH$_3$" (methylthiomethyl group) intervenes between two carbon atoms in an alkyl group having 2 carbon atoms. A sulfur atom or the like intervening between one carbon atom and the phenyl group optionally having a substituent or between one carbon atom and a nitrogen atom to which $R^1$ is bonded is also similarly interpreted.

Examples of the "phenyl group optionally having a substituent" as $R^1$, $R^2$, $R^3$, or $R^4$ in Formula (1) include a phenyl group, a 2-methylphenyl group, a 3-methylphenyl group, a 4-methylphenyl group, a 2-ethylphenyl group, a 3-ethylphenyl group, a 4-ethylphenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2,3-dimethylphenyl group, a 2,3-difluorophenyl group, a 2-methyl-4-fluorophenyl group, 2-amino-5-fluorophenyl group, a 2-ethyl-6-fluorophenyl group, a 3-ethyl-4-methoxyphenyl group, 3-ethyl-5-fluorophenyl group, a 2,3,5-trimethylphenyl group, a 2,4,6-trifluorophenyl group, a 2,3-dimethyl-4-fluorophenyl group, a 2-bromo-3-fluoro-5-methylphenyl group, a 2-methoxy-3-fluoro-6-(dimethylamino)phenyl group, a 2-(methylamino)-4-fluoro-6-methylphenyl group, a 2,3,4,5-tetramethylphenyl group, 2,3,4,6-tetrafluorophenyl group, 2,3-dimethyl-4,5-difluorophenyl group, 2-ethoxy-3-methyl-4-fluoro-6-(dimethylamino)phenyl group, 2-bromo-3,5-difluoro-6-(dimethylamino)phenyl group, and 2,3,4,5,6-pentafluorophenyl group. Among these, from the viewpoint of forming a rigid SEI, $R^1$, $R^2$, $R^3$, and $R^4$ each independently may be a phenyl group, a 2-fluorophenyl group, a 3-fluorophenyl group, or a 4-fluorophenyl group.

Examples of the "alkyl group having 1 to 6 carbon atoms which is substituted with a phenyl group optionally having a substituent" as $R^1$, $R^2$, $R^3$, or R include a phenylalkyl group such as —CH$_2$Ph (benzyl group), —CH$_2$CH$_2$Ph (phenethyl group), —CH(CH$_3$)Ph, —CH$_2$CH$_2$CH$_2$Ph (3-phenylpropyl group), —CH(CH$_3$)CH$_2$Ph, —CH(Ph)CH$_2$CH$_3$, —CH$_2$CH(CH$_3$)Ph, —CH$_2$(2-FPh), —CH$_2$(2,3-F$_2$Ph), —CH$_2$(2,4,6-F$_3$Ph), —CH$_2$(2,3,4,5-F$_4$Ph), —CH$_2$(2,3,4,5,6-F$_5$Ph), —CH$_2$CH—CH(CH$_3$)CH$_2$(4-FPh), —CH(3-FPh)CH$_2$CH$_2$(3-FPh), —CHCH$_3$(4-FPh), —CH$_2$CH$_2$CH$_2$(2-FPh), —CH$_2$CH(CH$_3$)(3-FPh), —CH$_2$(3-CH$_3$Ph), —CH$_2$[2,3-(CH$_3$)$_2$Ph], —CH$_2$[2,3,4-(CH$_3$)$_3$Ph], —CH$_2$CH$_2$(4-CH$_3$Ph), —CH$_2$CH$_2$[2,4-(CH$_3$)$_2$Ph], —CH$_2$CH$_2$[2,4,6-(CH$_3$)$_3$Ph], —CH(CH$_3$)(2-CH$_3$Ph), —CH$_2$CH$_2$CH$_2$(3-CH$_3$Ph), —CH(CH$_3$)CH$_2$(3-CH$_3$Ph), —CH(2-CH$_3$Ph)CH$_2$CH$_3$, and —CH$_2$CH(CH$_3$)(4-CH$_3$Ph). In the notations of these groups, "2-FPh" refers to a 2-fluorophenyl, "2,3-F$_2$Ph" refers to a 2,3-difluorophenyl, "2,4,6-F$_3$Ph" refers to a 2,4,6-trifluorophenyl, "2,3,4,5-F$_4$Ph" refers to a 2,3,4,5-tetrafluorophenyl, "2,3,4,5,6-F$_5$Ph" refers to a 2,3,4,5,6-pentafluorophenyl. In addition, "4-FPh", "3-CH$_3$Ph", and the like also similarly refer to 4-fluorophenyl, 3-methylphenyl, and the like, respectively.

In the "alkyl group having 1 to 6 carbon atoms which is substituted with a phenyl group optionally having a substituent" as $R^1$, $R^2$, $R^3$, or $R^4$ in Formula (1), examples of the substituent, which the "phenyl group optionally having a substituent" may have, include a halogen atom, —OCH$_3$, —SCH$_3$, —NH$_2$, NHCH$_3$, —N(CH$_3$)$_2$, —CH$_3$, and —CH$_2$CH$_3$. The substituent which the phenyl group may have is suitably a halogen atom, a methyl group, or an ethyl group. In a case where the number of carbon atoms in the substituent of the phenyl group increases, solubility thereof in an electrolyte solution may decrease.

$R^1$ may be, in particular, a group selected from groups represented by Formula (2). In Formula (2), (*) indicates a site bonded to a nitrogen atom. Among these, from the viewpoint of ease of reaction and performance, a benzyl group is more preferable.

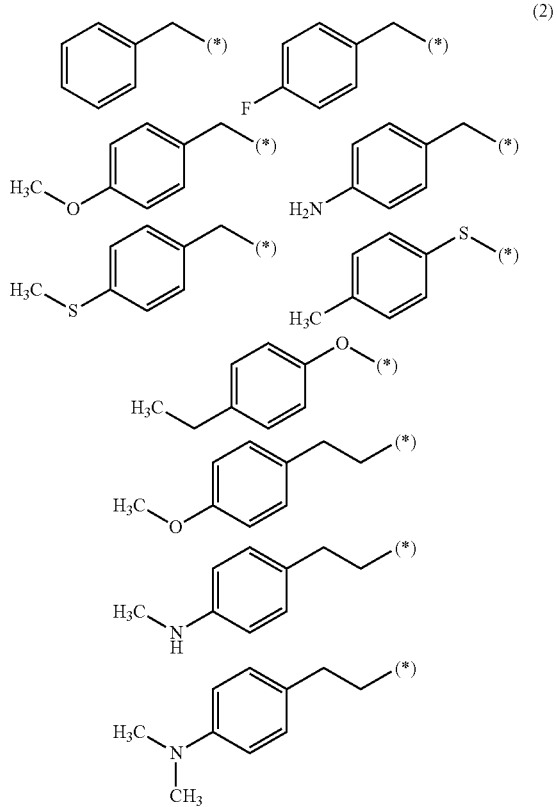

(2)

Examples of the "alkyl group having 1 to 6 carbon atoms which may be substituted with a phenyl group optionally having a substituent" as $R^2$, $R^3$, or $R^4$, in which a sulfur atom intervenes between two carbon atoms of the alkyl group or between one carbon atom of the alkyl group and a nitrogen atom to which $R^2$, $R^3$, or $R^4$ is bonded, include an alkylthio group such as —SCH$_3$, —SCH$_2$CH$_3$, —SCH$_2$CH$_2$CH$_3$, —SCH(CH$_3$)$_2$, —CH(SCH$_3$)$_2$, —SCH$_2$CH$_2$CH$_2$CH$_3$, —SCH(CH$_3$)CH$_2$CH$_3$, and —SCH$_2$CH(CH$_3$)$_2$; and an alkylthioalkyl group such as —CH$_2$SCH$_3$, —CH$_2$SCH$_2$CH$_3$, —CH$_2$CH$_2$SCH$_3$, —CH$_2$SCH$_2$CH$_2$CH$_3$, —CH$_2$CH$_2$SCH$_2$CH$_3$, —CH$_2$CH$_2$CH$_2$SCH$_3$, —CH(SCH$_3$)CH$_2$CH$_3$, —CH(CH$_3$)SCH$_2$CH$_3$, —CH(CH$_3$)CH$_2$SCH$_3$, —CH$_2$SCH(CH$_3$)$_2$, and —CH$_2$CH(SCH$_3$)$_2$.

Examples of the "alkyl group having 1 to 6 carbon atoms which may be substituted with a phenyl group optionally having a substituent" as $R^2$, $R^3$, or $R^4$, in which an oxygen atom intervenes between two carbon atoms of the alkyl group or between one carbon atom of the alkyl group and a nitrogen atom to which $R^2$, $R^3$, or $R^4$ is bonded, include an alkoxy group such as —OCH$_3$, —OCH$_2$CH$_3$, —OCH$_2$CH$_2$CH$_3$, —OCH$_2$CH$_2$CH$_2$CH$_3$, —OCH(CH$_3$)CH$_2$CH$_3$, and —OCH$_2$CH(CH$_3$)$_2$; and an alkoxyalkyl group such as —CH$_2$OCH$_3$, —CH$_2$OCH$_2$CH$_3$, —CH$_2$CH$_2$OCH$_3$, —OCH(CH$_3$)$_2$, —CH(OCH$_3$)$_2$, —CH$_2$OCH$_2$CH$_2$CH$_3$, —CH$_2$CH$_2$OCH$_2$CH$_3$, —CH$_2$CH$_2$CH$_2$OCH$_3$, —CH(OCH$_3$)CH$_2$CH$_3$, —CH(CH$_3$)OCH$_2$CH$_3$, —CH(CH$_3$)CH$_2$OCH$_3$, —CH$_2$OCH(CH$_3$)$_2$, and —CH$_2$CH(OCH$_3$)$_2$.

Examples of the "alkyl group having 1 to 6 carbon atoms which may be substituted with a phenyl group optionally having a substituent" as $R^2$, $R^3$, or $R^4$, in which an amino group optionally having a substituent (such as a phenyl group) intervenes between two carbon atoms of the alkyl group or between one carbon atom of the alkyl group and a nitrogen atom to which $R^2$, $R^3$, or $R^4$ is bonded, include an N-alkylamino group such as —NHCH$_3$, —NHCH$_2$CH$_3$, —NHCH$_2$CH$_2$CH$_3$, —NHCH(CH$_3$)$_2$, —NHCH$_2$CH$_2$CH$_2$CH$_3$, —NHCH(CH$_3$)CH$_2$CH$_3$, —NHCH$_2$CH(CH$_3$)$_2$, —N(CH$_3$)CH$_3$, N—(CH$_3$)CH$_2$CH$_3$, —N(CH$_3$)CH$_2$CH$_2$CH$_3$, —N(CH$_3$)CH(CH$_3$)$_2$, —N(CH$_3$)CH$_2$CH$_2$CH$_2$CH$_3$, —N(CH$_3$)CH(CH$_3$)CH$_2$CH$_3$, and —N(CH$_3$)CH$_2$CH(CH$_3$)$_2$; an alkylaminoalkyl group such as —CH$_2$NHCH$_3$, —CH$_2$NHCH$_2$CH$_3$, —CH$_2$CH$_2$NHCH$_3$, —CH(NHCH$_3$)$_2$, —CH$_2$NHCH$_2$CH$_3$, —CH$_2$CH$_2$NHCH$_2$CH$_3$, —CH$_2$CH$_2$CH$_2$NHCH$_3$, —CH(CH$_3$)NHCH$_2$CH$_3$, —CH(CH$_3$)CH$_2$NHCH$_3$, —CH$_2$NHCH(CH$_3$)$_2$, —CH$_2$CH(NHCH$_3$)$_2$, —CH$_2$N(CH$_3$)CH$_3$, —CH$_2$N(CH$_3$)CH$_2$CH$_3$, CH$_2$CH$_2$N(CH$_3$)CH$_3$, —CH(N(CH$_3$)CH$_3$)$_2$, —CH$_2$N(CH$_3$)CH$_2$CH$_2$CH$_3$, —CH$_2$CH$_2$N(CH$_3$)CH$_2$CH$_3$, —CH$_2$CH$_2$CH$_2$N(CH$_3$)CH$_3$, —CH(N(CH$_3$)CH$_3$)$_2$CH$_2$CH$_3$, —CH(CH$_3$)N(CH$_3$)CH$_2$CH$_3$, —CH(CH$_3$)CH$_2$N(CH$_3$)CH$_3$, —CH$_2$N(CH$_3$)CH(CH$_3$)$_2$, and —CH$_2$CH(N(CH$_3$)CH$_3$)$_2$; an N-phenyl-N-alkylamino group such as —N(Ph)CH$_3$, —N(Ph)CH$_2$CH$_3$, —N(Ph)CH$_2$CH$_2$CH$_3$, —N(Ph)CH(CH$_3$)$_2$, —N(Ph)CH$_2$CH$_2$CH$_2$CH$_3$, —N(Ph)CH(CH$_3$)CH$_2$CH$_3$, and —N(Ph)CH$_2$CH(CH$_3$)$_2$; and a phenylaminoalkyl group such as —CH$_2$N(Ph)CH$_3$, —CH$_2$N(Ph)CH$_2$CH$_3$, —CH$_2$CH$_2$N(Ph)CH$_3$, —CH(N(Ph)CH$_3$)$_2$, —CH$_2$N(Ph)CH$_2$CH$_2$CH$_3$, —CH$_2$CH$_2$N(Ph)CH$_2$CH$_3$, —CH$_2$CH$_2$CH$_2$N(Ph)CH$_3$, —CH(N(Ph)CH$_3$)CH$_2$CH$_3$, —CH(CH$_3$)N(Ph)CH$_2$CH$_3$, —CH(CH$_3$)CH$_2$N(Ph)CH$_3$, —CH$_2$N(Ph)CH(CH$_3$)$_2$, and —CH$_2$CH(N(Ph)CH$_3$)$_2$. Suitably, a group selected from a phenyl group, a halogen atom, a methyl group, and an ethyl group is bonded to the amino group. In a case where the number of carbon atoms in a group bonded to the amino group increases, solubility thereof in an electrolyte solution may decrease.

Examples of an unsubstituted alkyl group having 1 to 6 carbon atoms as $R^2$, $R^3$, or $R^4$ in Formula (1) include a methyl group, an ethyl group, an n-propyl group, an isopropyl group, an n-butyl group, a 1-methylethyl group, an n-pentyl group, and an n-hexyl group.

In Formula (1), $R^2$, $R^3$, and $R^4$ are preferably each independently a phenyl group, a benzyl group, a phenethyl group, a 3-phenylpropyl group, a monofluorophenyl group, a difluorophenyl group, a monofluorobenzyl group, a difluorobenzyl group, a methylphenyl group, a dimethylphenyl group, a methylbenzyl group, or a dimethylbenzyl group, and are more preferably each independently a phenyl group, a benzyl group, a monofluorophenyl group, or a monofluorobenzyl group.

In Formula (1), it is particularly preferable that $R^3$ and $R^1$ are the same group, and $R^2$ and $R^4$ are the same group. More preferably, from the viewpoint of solubility of the disulfonic acid amide compound, $R^1$ and $R^3$ are both a phenyl group optionally having a substituent, in which the substituent is an alkyl group having 1 to 2 carbon atoms or a halogen atom, or $R^1$ and $R^3$ are both an alkyl group having 1 to 6 carbon atoms optionally substituted with a phenyl group. Even more preferably, $R^1$ and $R^3$ are both a phenyl group, and $R^2$ and $R^4$ are both a hydrogen atom; $R^1$ and $R^3$ are both a phenyl group, and $R^2$ and $R^4$ are both a methyl group; $R^1$ and $R^3$ are both a benzyl group, and $R^2$ and $R^4$ are both a methyl group; $R^1$ and $R^3$ are both a benzyl group, and $R^2$ and $R^4$ are both a benzyl group; or $R^1$ and $R^3$ are both a fluorophenyl group, and, $R^2$ and $R^4$ are both a hydrogen atom.

In Formula (1), $R^1$ and $R^2$ may be linked to form an alkylene group having 2 to 5 carbon atoms in total which forms a cyclic structure together with a nitrogen atom to which they are bonded. In Formula (1), $R^3$ and $R^4$ may also be linked to form an alkylene group having 2 to 5 carbon atoms in total which forms a cyclic structure together with a nitrogen atom to which they are bonded. In the alkylene group as $R^1$ and $R^2$, or $R^3$ and $R^4$, a sulfur atom, an oxygen atom, or an amino group optionally having a substituent may intervene between two carbon atoms thereof, or between one carbon atom thereof and a nitrogen atom to which $R^1$ and $R^2$, or $R^3$ and $R^4$ are bonded.

Examples of the "alkylene group having 2 to 5 carbon atoms in total", which may be formed by linkage of $R^1$ and $R^2$ in Formula (1), include —O—$(CH_2)_2$—, —O—$(CH_2)_3$—, —O—$(CH_2)_4$—, —O—$(CH_2)_5$—, —$CH_2$—O—$CH_2$—, —$CH_2$—O—$(CH_2)_2$—, —$CH_2$—O—$(CH_2)_3$—, —$CH_2$—O—$(CH_2)_4$—, —$(CH_2)_2$—O—$(CH_2)_2$—, —$(CH_2)_2$—O—$(CH_2)_3$—, —N—$(CH_2)_2$—, —N—$(CH_2)_3$—, —N—$(CH_2)_4$—, —N—$(CH_2)_5$—, —$CH_2$—N—$CH_2$—, —$CH_2$—N—$(CH_2)_2$—, —$CH_2$—N—$(CH_2)_3$—, —$CH_2$—N—$(CH_2)_4$—, —$(CH_2)_2$—N—$(CH_2)_2$—, —$(CH_2)_2$—N—$(CH_2)_3$—, —N$(CH_3)$—$CH_2$—, —N$(CH_3)$—$(CH_2)_2$—, —N$(CH_3)$—$(CH_2)_3$—, —N$(CH_3)$—$(CH_2)_4$—, —N$(CH_3)$—$(CH_2)_5$—, —$CH_2$—N$(CH_3)$—$CH_2$—, —$CH_2$—N$(CH_3)$—$(CH_2)_2$—, —$CH_2$—N$(CH_3)$—$(CH_2)_3$—, —$CH_2$—N$(CH_3)$—$(CH_2)_4$—, —$(CH_2)_2$—N$(CH_3)$—$(CH_2)_2$—, —$(CH_2)_2$—N$(CH_3)$—$(CH_2)_3$—, —S—$(CH_2)_2$—, —S—$(CH_2)_3$—, —S—$(CH_2)_4$—, —S—$(CH_2)_5$—, —$CH_2$—S—$CH_2$—, —$CH_2$—S—$(CH_2)_2$—, —$CH_2$—S—$(CH_2)_3$—, —$CH_2$—S—$(CH_2)_4$—, —$(CH_2)_2$—S—$(CH_2)_2$—, —$(CH_2)_2$—S—$(CH_2)_3$—, —$(CH_2)_2$—, —$(CH_2)_3$—, —$(CH_2)_4$—, and —$(CH_2)_5$—. The number of carbon atoms in the alkylene group is more suitably 3 to 5. In that case, the "alkylene group having 2 to 5 carbon atoms in total" is more suitably —$(CH_2)_2$—O—$(CH_2)_2$—, —$(CH_2)_2$—NH—$(CH_2)_2$—, —$(CH_2)_2$—N$(CH_3)$—$(CH_2)_2$—, —$(CH_2)_2$—S—$(CH_2)_2$—, —$(CH_2)_4$—, or —$(CH_2)_5$—.

In Formula (1), the cyclic structure that may be formed by linkage of $R^1$ and $R^2$, or $R^3$ and $R^4$ together with a nitrogen atom to which they are bonded, is preferably a 5- or 6-membered ring. In a case where such cyclic structure is a 4 or less-membered ring, it may be difficult to produce the cyclic structure. Such cyclic structure is preferably a piperidine ring, a morpholine ring, a thiomorpholine ring, or a methylpiperazine ring.

Examples of the disulfonic acid amide compound represented by Formula (1) include difluoromethane disulfonic acid bis-phenylamide, difluoromethane disulfonic acid bis-methylphenylamide, difluoromethane disulfonic acid bis-benzylamide, difluoromethane disulfonic acid bis-dibenzylamide, difluoromethane disulfonic acid bis-methylbenzylamide, difluoromethane disulfonic acid bis-benzylphenylamide, difluoromethane disulfonic acid bis-(2-fluorophenylamide), difluoromethane disulfonic acid bis-(2-fluorophenylamide), difluoromethane disulfonic acid bis-(2-fluorophenylamide), difluoromethane disulfonic acid bis-pyrrolidine, difluoromethane disulfonic acid bis-piperidine, difluoromethane disulfonic acid bis-morpholine, difluoromethane disulfonic acid bis-thiomorpholine, 1,2-difluoroethane disulfonic acid bis-morpholine, difluoromethane disulfonic acid bis-(1-methylpiperazine), 1,1-difluoroethane disulfonic acid bis-morpholine, 1,1,2-trifluoroethane disulfonic acid bis-morpholine, 1,1,2,2-tetrafluoroethane disulfonic acid bis-morpholine, fluoromethane disulfonic acid bis-phenylamide, fluoromethane disulfonic acid bis-methylphenylamide, fluoromethane disulfonic acid bis-benzylamide, fluoromethane disulfonic acid bis-dibenzylamide, fluoromethane disulfonic acid bis-methylbenzylamide, fluoromethane disulfonic acid bis-benzylphenylamide, fluoromethane disulfonic acid bis-(2-fluorophenylamide), fluoromethane disulfonic acid bis-(2-fluorophenylamide), difluoromethane disulfonic acid bis-(4-fluorophenylamide), fluoromethane disulfonic acid bis-pyrrolidine, fluoromethane disulfonic acid bis-piperidine, fluoromethane disulfonic acid bis-morpholine, fluoromethane disulfonic acid bis-thiomorpholine, 1-fluoroethane disulfonic bismorpholine, fluoromethane disulfonic acid bis-(1-methylpiperazine), and 1,1-fluoroethane disulfonic acid bis-morpholine.

Among these, from the viewpoint that the generation of gases is further suppressed, compounds having 2 or more fluorine atoms are preferable. Examples thereof include difluoromethane disulfonic acid bis-phenylamide, difluoromethane disulfonic acid bis-methylphenyl amide, difluoromethane disulfonic acid bis-benzylamide, difluoromethane disulfonic acid bis-dibenzylamide, difluoromethane disulfonic acid bis-methylbenzylamide, difluoromethane disulfonic acid bis-benzylphenylamide, difluoromethane disulfonic acid bis-(2-fluorophenylamide), difluoromethane disulfonic acid bis-(4-fluorophenylamide), difluoromethane disulfonic acid bis-pyrrolidine, difluoromethane disulfonic acid bis-piperidine, difluoromethane disulfonic acid bis-morpholine, difluoromethane disulfonic acid bis-thiomorpholine, 1,2-difluoroethane disulfonic acid bis-morpholine, difluoromethane disulfonic acid bis-(1-methylpiperazine), 1,1-difluoroethane disulfonic acid bis-morpholine, 1,1,2-trifluoroethane disulfonic acid bis-morpholine, and 1,1,2,2-tetrafluoroethane disulfonic acid bis-morpholine.

Examples of a method for producing a disulfonic acid amide compound represented by Formula (1) include a method comprising reacting methane disulfonyl chloride with a primary or secondary amine to obtain disulfonic acid amide and introducing a halogen atom into an alkylene group in the resulting disulfonic acid amide using a halogenating agent in the presence of sodium hydride. In addition, examples of a method for producing difluoromethane disulfonic acid bis-morpholine include a method comprising reacting morpholine with methane disulfonyl chloride, then reacting the mixture by dropwise addition of triethylamine to obtain methane disulfonic acid bis-morpholine, and then introduce a halogen atom into this methane disulfonic acid bis-morpholine using a halogenating agent in the presence of sodium hydride. In these production methods, it is also possible to use a reaction solvent such as 1,2-dimethoxyethane or tetrahydrofuran, if necessary.

The disulfonic acid amide compound represented by Formula (1) exhibits low LUMO energy, which makes susceptible to electrochemical reduction. Thus, in a case where the additive for nonaqueous electrolyte solutions which contains the compound is contained in a nonaqueous electrolyte solution and used in an electricity storage device such as a nonaqueous electrolyte solution secondary battery, the additive can form a stable SEI on the surface of an electrode to improve battery characteristics such as cycle characteristics, a charge/discharge capacity, internal resistance and gas generation. Further, since the disulfonic acid amide compound represented by Formula (1) is stable against moisture and temperature changes, an additive for nonaqueous electrolyte solutions which contains the compound, can be stored at room temperature for a long period of time. Therefore, a nonaqueous electrolyte solution containing the additive for nonaqueous electrolyte solutions can also withstand a long-term storage and use.

A nonaqueous electrolyte solution according to one embodiment contains the additive for nonaqueous electrolyte solutions, a nonaqueous solvent, and an electrolyte.

For a content of the additive for nonaqueous electrolyte solutions in the nonaqueous electrolyte solution of the present embodiment (that is, content of the disulfonic acid amide compound represented by Formula (1)), a preferable lower limit thereof is 0.005% by mass and a preferable upper limit thereof is 10% by mass. The content here is a percentage in a case where the total mass of the nonaqueous solvent and the electrolyte is set as 100% by mass. If the content of the additive for nonaqueous electrolyte solutions is less than 0.005% by mass, there is a tendency that the effect of forming a stable SEI on the surface of an electrode in a nonaqueous electrolyte solution secondary battery or the like due to an electrochemical reduction reaction becomes relatively small. If the content of the additive for nonaqueous electrolyte solutions exceeds 10% by mass, there is a tendency that the viscosity of the nonaqueous electrolyte solution increases and thus it is difficult to secure the ion mobility. Therefore, it may be difficult to sufficiently secure the electrical conductivity or the like of the electrolyte solution and charge/discharge characteristics or the like of an electricity storage device such as a nonaqueous electrolyte solution secondary battery may be relatively lowered. A more preferable lower limit of the content of the additive for nonaqueous electrolyte solutions is 0.01% by mass. The additives for nonaqueous electrolyte solutions (that is, disulfonic acid amide compounds represented by Formula (1)) may be used alone or in combination of two or more kinds thereof. In a case where the compounds are used in combination of two or more kinds, for the total content of the compounds, a preferable lower limit thereof is 0.005% by mass, and a preferable upper limit thereof is 10% by mass.

The disulfonic amide compound represented by Formula (1) may be used in combination with a common additive such as vinylene carbonate (VC), fluoroethylene carbonate (FEC), and 1,3-propanesultone (PS), if necessary, in a nonaqueous electrolyte solution.

As the nonaqueous solvent constituting the nonaqueous electrolyte solution, from the viewpoint of suppressing the viscosity of the nonaqueous electrolyte solution to be obtained to a lower value, an aprotic solvent is suitable. Among these, the nonaqueous solvent is preferably at least one selected from the group consisting of a cyclic carbonate, a chained carbonate, an aliphatic carboxylic acid ester, a lactone, a lactam, a cyclic ether, a chained ether, a sulfone, and a halogen derivative thereof. Among these, a cyclic carbonate, a chained carbonate, or a combination thereof is more preferably used.

Examples of the cyclic carbonate include ethylene carbonate, propylene carbonate, and butylene carbonate.

Examples of the chained carbonate include dimethyl carbonate, diethyl carbonate, and ethylmethyl carbonate.

Examples of the aliphatic carboxylic acid ester include methyl acetate, ethyl acetate, methyl propionate, ethyl propionate, methyl butyrate, methyl isobutyrate, and methyl trimethylacetate.

Examples of the lactone include γ-butyrolactone.

Examples of the lactam include ε-caprolactam and N-methylpyrrolidone.

Examples of the cyclic ether include tetrahydrofuran, 2-methyltetrahydrofuran, tetrahydropyran, and 1,3-dioxolane.

Examples of the chained ether include 1,2-diethoxyethane and ethoxymethoxyethane.

Examples of the sulfone include sulfolane.

Examples of the halogen derivative include 4-fluoro-1,3-dioxolan-2-one, 4-chloro-1,3-dioxolan-2-one, and 4,5-difluoro-1,3-dioxolan-2-one.

These nonaqueous solvents may be used alone or in admixture of plural kinds thereof. These nonaqueous solvents are, for example, preferably used in nonaqueous electrolyte solution secondary batteries such as a lithium ion battery, or electric double layer capacitors such as a lithium ion capacitor.

The electrolyte constituting the nonaqueous electrolyte solution is preferably a lithium salt which serves as an ion source of lithium ions. Among these, the electrolyte may be preferably at least one selected from the group consisting of $LiAlCl_4$, $LiBF_4$, $LiPF_6$, $LiClO_4$, $LiAsF_6$, and $LiSbF_6$. The electrolyte is preferably $LiBF_4$ and/or $LiPF_6$ from the viewpoints that, for example, they have a high degree of dissociation and thus are capable of increasing the ion conductivity of the electrolyte solution, and also have an action of suppressing deterioration of the performance of an electricity storage device by a long-term use due to their oxidation-reduction resistance characteristics. These electrolytes may be used alone or in combination of two or more kinds thereof.

For the concentration of the electrolyte in the nonaqueous electrolyte solution, a preferable lower limit thereof is 0.1 mol/L, and a preferable upper limit thereof is 2.0 mol/L. The concentration of the electrolyte here is a value based on the volume of the nonaqueous solvent. If the concentration of the electrolyte is less than 0.1 mol/L, it may be difficult to sufficiently secure the electrical conductivity or the like of the nonaqueous electrolyte solution, and charge characteristics, discharge characteristics, and the like of an electricity storage device such as a nonaqueous electrolyte solution secondary battery may be relatively lowered. If the concentration of the electrolyte exceeds 2.0 mol/L, there is a tendency that the viscosity of the nonaqueous electrolyte solution increases and thus it is difficult to sufficiently secure the ion mobility. Therefore, it may be difficult to sufficiently secure the electrical conductivity or the like of the nonaqueous electrolyte solution, and charge characteristics, discharge characteristics, and the like of an electricity storage device such as a nonaqueous electrolyte solution secondary battery may be relatively lowered. For the concentration of the electrolyte, a more preferable lower limit thereof is 0.5 mol/L, and a more preferable upper limit thereof is 1.5 mol/L.

An electricity storage device according to one embodiment includes a nonaqueous electrolyte solution, a positive electrode, and a negative electrode. Examples of the electricity storage device include nonaqueous electrolyte solution secondary batteries and electric double layer capacitors. Among these, a lithium ion battery or a lithium ion capacitor is suitable.

FIG. 1 is a cross-sectional view schematically showing an embodiment of a nonaqueous electrolyte solution secondary battery as an example of an electricity storage device. A nonaqueous electrolyte solution secondary battery 1 shown in FIG. 1 includes a positive electrode plate 4 having a positive electrode collector 2 and a positive electrode active material layer 3 provided on one side of the positive electrode collector 2, and a negative electrode plate 7 having a negative electrode collector 5 and a negative electrode active material layer 6 provided on one side of the negative electrode collector 5. The positive electrode plate 4 and the negative electrode plate 7 are disposed to face each other through a separator 9 provided in a nonaqueous electrolyte solution 8 and a nonaqueous electrolyte solution 8. As the nonaqueous electrolyte solution 8, the nonaqueous electrolyte solution according to the above-mentioned embodiment can be used.

As the positive electrode collector 2 and the negative electrode collector 5, for example, a metal foil formed of a metal selected from aluminum, copper, nickel, and stainless steel can be used.

As the positive electrode active material used for the positive electrode active material layer 3, a lithium-containing composite oxide is preferable. Examples thereof include a lithium-containing composite oxide such as $LiMnO_2$, $LiFeO_2$, $LiCoO_2$, $LiMn_2O_4$, $Li_2FeSiO_4$, $LiNi_{1/3}Co_{1/3}Mn_{1/3}O_2$, and $LiFePO_4$.

Examples of the negative electrode active material used for the negative electrode active material layer 6 include a material capable of absorbing and releasing lithium. Examples of such a material include carbon materials such as graphite and amorphous carbon, and oxide materials such as indium oxide, silicon oxide, tin oxide, zinc oxide, and lithium oxide. As the negative electrode active material, a lithium metal and a metal material capable of forming an alloy with lithium can be used. Examples of the metal capable of forming an alloy with lithium include Cu, Sn, Si, Co, Mn, Fe, Sb, and Ag. A binary or ternary alloy including any of these metals and lithium can also be used as the negative electrode active material. These negative electrode active materials may be used alone or in combination of two or more kinds thereof.

As the separator 9, for example, a porous film formed of polyethylene, polypropylene, fluorine resins, or the like can be used.

EXAMPLES

The invention will be described below in more detail with reference to Examples. The invention is not limited to these Examples.

Nonaqueous Electrolyte Solution

Example 1

Preparation of Difluoromethane Disulfonic Acid Bis-Phenylamide (Compound 1)

Into a 200 mL four-neck flask equipped with a stirrer, a condenser, a thermometer, and a dropping funnel, 10.2 g (0.11 mol) of aniline and 100 g of 1,2-dimethoxyethane were charged. Thereinto, 10.7 g (0.05 mol) of methane disulfonyl chloride dissolved in 10 g of 1,2-dimethoxyethane was added dropwise over 20 minutes while maintaining the reaction solution at 0° C. Subsequently, while maintaining the reaction solution at the same temperature, 11.1 g (0.11 mol) of triethylamine dissolved in 10 g of 1,2-dimethoxyethane was added dropwise over 1 hour. Thereafter, the reaction was allowed to proceed by stirring the reaction solution for 8 hours while maintaining it at the same temperature.

After completion of the reaction, the reaction solution was filtered. Liquid separation was performed by adding 100.0 g of toluene and 50.0 g of water to the resulting filtrate. A portion of the solvent was distilled off under reduced pressure at 25° C. from the resulting organic layer to precipitate crystals, and the precipitated crystals were collected by filtration. The resulting crystals were dried to obtain 11.1 g (0.034 mol) of methane disulfonic acid bis-phenylamide (Compound 11). The yield of methane disulfonic acid bis-phenylamide was 68.0% relative to methane disulfonyl chloride.

Subsequently, into a 500 mL four-neck flask equipped with a stirrer, a condenser, a thermometer, and a dropping funnel, 2.6 g (0.07 mol) of sodium hydride and 150 g of tetrahydrofuran were charged. Thereinto, 9.8 g (0.03 mol) of methane disulfonic acid bis-phenylamide dissolved in 50 g of tetrahydrofuran was added dropwise over 20 minutes while maintaining the reaction solution at 5° C. Subsequently, while maintaining the reaction solution at the same temperature, 23.4 g (0.07 mol) of N-fluoro-N'-(chloromethyl)triethylenediamine bis-(tetrafluoroborate) was added over 10 minutes. Further, the reaction was allowed to proceed by stirring the reaction solution for 1 hour while maintaining it at the same temperature and then increasing the temperature to 25° C. and stirring it for 10 hours.

After completion of the reaction, liquid separation was performed by adding 100 g of ethyl acetate and 60 g of saturated aqueous ammonium chloride solution to obtain an organic layer. 50 g of saturated saline was added to the resulting organic layer and liquid separation was performed to obtain an organic layer. After adding 5 g of magnesium sulfate to this organic layer and stirring the mixture at room temperature for 30 minutes, magnesium sulfate was removed by filtration. A portion of the solvent was distilled off under reduced pressure at 30° C. from the resulting filtrate and then heptane was added dropwise to precipitate crystals. The crystals were collected by filtration and dried to obtain 8.0 g (0.022 mol) of difluoromethane disulfonic acid bis-phenylamide (Compound 1). The yield of difluoromethane disulfonic acid bis-phenylamide was 73.3% relative to methane disulfonyl chloride.

Preparation of Nonaqueous Electrolyte Solution

In a mixed nonaqueous solvent obtained by mixing ethylene carbonate (EC) and diethyl carbonate (DEC) at a volume ratio of EC:DEC=30:70, $LiPF_6$ as an electrolyte was dissolved so that a concentration thereof is 1.0 mol/L. To the resulting solution, Compound 1 as an additive for nonaqueous electrolyte solutions was added so that the content of the additive was 0.5% by mass with respect to the total mass of the mixed nonaqueous solvent and the electrolyte, thereby preparing a nonaqueous electrolyte solution.

Example 2

A nonaqueous electrolyte solution was prepared in the same manner as in Example 1 except that the content of Compound 1 was set to 1.0% by mass in the "Preparation of Nonaqueous Electrolyte Solution".

Example 3

Preparation of Difluoromethane Disulfonic Acid Bis-Methylphenylamide (Compound 2)

13.5 g (0.038 mol) of methane disulfonic acid bis-methylphenylamide (Compound 12) was obtained in the same manner as in Example 1 except that 10.2 g (0.11 mol) of aniline was changed to 11.8 g (0.11 mol) of N-methyl-N-phenylamine. The yield of methane disulfonic acid bis-methylphenylamide was 76.1% relative to methane disulfonyl chloride.

Subsequently, 7.4 g (0.019 mol) of difluoromethane disulfonic acid bis-methylphenylamide (Compound 2) was obtained in the same manner as in Example 1 except that 9.8 g (0.03 mol) of methane disulfonic acid bis-phenylamide was changed to 10.6 g (0.03 mol) of methane disulfonic acid bis-methylphenylamide. The yield of difluoromethane disulfonic acid bis-methylphenylamide was 63.3% relative to methane disulfonic acid bis-methylphenylamide.

Preparation of Nonaqueous Electrolyte Solution

A nonaqueous electrolyte solution was prepared in the same manner as in Example 1 except that Compound 2 was used in place of Compound 1 and the content thereof was set to 1.0% by mass in the "Preparation of Nonaqueous Electrolyte Solution".

Example 4

Preparation of Difluoromethane Disulfonic Acid Bis-Methylbenzylamide (Compound 3)

12.9 g (0.034 mol) of methane disulfonic acid bis-methylbenzylamide (Compound 13) was obtained in the same manner as in Example 1 except that 10.2 g (0.11 mol) of aniline was changed to 13.3 g (0.11 mol) of N-methyl-N-benzylamine. The yield of methane disulfonic acid bis-methylbenzylamide was 67.5% relative to methane disulfonyl chloride.

Then, 7.9 g (0.021 mol) of difluoromethane disulfonic acid bis-methylbenzylamide (Compound 3) was obtained in the same manner as in Example 1 except that 9.8 g (0.03 mol) of methane disulfonic acid bis-phenylamide was changed to 11.5 g (0.03 mol) of methane disulfonic acid bis-methylbenzylamide. The yield of difluoromethane disulfonic acid bis-methylbenzylamide was 68.8% relative to methane disulfonic acid bis-methylbenzylamide.

Preparation of Nonaqueous Electrolyte Solution

A nonaqueous electrolyte solution was prepared in the same manner as in the "Preparation of Nonaqueous Electrolyte Solution" of Example 1 except that Compound 3 was used in place of Compound 1 and the content thereof was set to 1.0% by mass.

Example 5

Preparation of Difluoromethane Disulfonic Acid Bis-Dibenzylamide (Compound 4)

16.9 g (0.032 mol) of methane disulfonic acid bis-dibenzylamide (Compound 14) was obtained in the same manner as in Example 1 except that 10.2 g (0.11 mol) of aniline was changed to 21.7 g (0.11 mol) of N, N-dibenzylamine. The yield of methane disulfonic acid bis-dibenzylamide was 63.2% relative to methane disulfonyl chloride.

Subsequently, 9.8 g (0.018 mol) of difluoromethane disulfonic acid bis-dibenzylamide (Compound 4) was obtained in the same manner as in Example 1 except that 9.8 g (0.03 mol) of methane disulfonic acid bis-phenylamide was changed to 16.0 g (0.03 mol) of methane disulfonic acid bis-dibenzylamide. The yield of difluoromethane disulfonic acid bis-dibenzylamide was 61.1% relative to methane disulfonic acid bis-dibenzylamide.

Preparation of Nonaqueous Electrolyte Solution

A nonaqueous electrolyte solution was prepared in the same manner as in the "Preparation of Nonaqueous Electrolyte Solution" of Example 1 except that Compound 4 was used in place of Compound 1 and the content thereof was set to 1.0% by mass.

Example 6

Preparation of Difluoromethane Disulfonic Acid Bis-(4-fluorophenylamide) (Compound 5)

11.5 g (0.032 mol) of methane disulfonic acid bis-(4-fluoro phenylamide) (Compound 15) was obtained in the same manner as in Example 1 except that 10.2 g (0.11 mol) of aniline was changed to 12.2 g (0.11 mol) of N-4-fluorophenylamine. The yield of methane disulfonic acid bis-(4-fluorophenylamide) was 63.5% relative to methane disulfonyl chloride.

Subsequently, 7.5 g (0.021 mol) of difluoromethane disulfonic acid bis-(4-fluorophenylamide) (Compound 5) was obtained in the same manner as in Example 1 except that 9.8 g (0.03 mole) of methane disulfonic acid bis-phenylamide was changed to 10.9 g (0.03 mol) of methane disulfonic acid bis-(4-fluorophenylamide). The yield of difluoromethane disulfonic acid bis-(4-fluorophenylamide) was 69.0% relative to methane disulfonic acid bis-(4-fluorophenylamide).

Preparation of Nonaqueous Electrolyte Solution

A nonaqueous electrolyte solution was prepared in the same manner as in the "Preparation of Nonaqueous Electrolyte Solution" of Example 1 except that Compound 5 was used in place of Compound 1 and the content thereof was set to 1.0% by mass.

Example 7

Preparation of Difluoromethane Disulfonic Acid Bis-Morpholine (Compound 6)

12.9 g (0.041 mol) of methane disulfonic acid bis-morpholine (Compound 16) was obtained in the same manner as in Example 1 except that 10.2 g (0.11 mol) of aniline was changed to 9.6 g (0.11 mol) of morpholine. The yield of methane disulfonic acid bis-morpholine was 82.1% relative to methane disulfonyl chloride.

Then, 5.3 g of (0.015 mol) of difluoromethane disulfonic acid bis-morpholine (Compound 6) were obtained in the same manner as in Example 1 except that 9.8 g (0.03 mol) of methane disulfonic acid bis-phenylamide was changed to 9.4 g (0.03 mol) of methane disulfonic acid bis-morpholine. The yield of difluoromethane disulfonic acid bis-morpholine was 50.0% relative to methane disulfonic acid bis-morpholine.

Preparation of Nonaqueous Electrolyte Solution

A nonaqueous electrolyte solution was prepared in the same manner as in the "Preparation of Nonaqueous Electrolyte Solution" of Example 1 except that Compound 6 was used in place of Compound 1 and the content thereof was set to 1.0% by mass.

Example 8

Preparation of Difluoromethane Disulfonic Acid Bis-Piperidine (Compound 7)

10.9 g (0.035 mol) of methane disulfonic acid bis-piperidine (Compound 17) was obtained in the same manner as in Example 1 except that 10.2 g (0.11 mol) of aniline was changed to 9.4 g (0.11 mol) of piperidine. The yield of methane disulfonic acid bis-piperidine was 70.2% relative to methane disulfonyl chloride.

5.9 g (0.019 mol) of difluoromethane disulfonic acid bis-piperidine (Compound 7) was obtained in the same manner as in Example 1 except that 9.8 g (0.03 mol) of methane disulfonic acid bis-phenylamide was changed to 9.3 g (0.03 mol) of methane disulfonic acid bis-piperidine. The yield of difluoromethane disulfonic acid bis-piperidine was 63.4% relative to methane disulfonic acid bis-piperidine.

Preparation of Nonaqueous Electrolyte Solution

A nonaqueous electrolyte solution was prepared in the same manner as in the "Preparation of Nonaqueous Electrolyte Solution" of Example 1 except that Compound 7 was used in place of Compound 1 and the content thereof was set to 1.0% by mass.

Example 9

Preparation of Difluoromethane Disulfonic Acid Bis-Pyrrolidine (Compound 8)

9.2 g (0.033 mol) of methane disulfonic acid bis-pyrrolidine (Compound 18) was obtained in the same manner as in Example 1 except that 10.2 g (0.11 mol) of aniline was changed to 7.8 g (0.11 mol) of pyrrolidine. The yield of methane disulfonic acid bis-pyrrolidine was 65.2% relative to methane disulfonyl chloride.

Subsequently, 5.1 g (0.018 mol) of difluoromethane disulfonic acid bis-pyrrolidine (Compound 8) was obtained in the same manner as in Example 1 except that 9.8 g (0.03 mol) of methane disulfonic acid bis-phenylamide was changed to 8.5 g (0.03 mol) of methane disulfonic acid bis-pyrrolidine. The yield of difluoromethane disulfonic acid bis-pyrrolidine was 60.2% relative to methane disulfonic acid bis-pyrrolidine.

Preparation of Nonaqueous Electrolyte Solution

A nonaqueous electrolyte solution was prepared in the same manner as in the "Preparation of Nonaqueous Electrolyte Solution" of Example 1 except that Compound 8 was used in place of Compound 1 and the content thereof was set to 1.0% by mass.

Example 10

Preparation of 1,2-Difluoroethane Disulfonic Acid Bis-Morpholine (Compound 9)

10.2 g (0.031 mol) of ethane disulfonic acid bis-morpholine (Compound 19) was obtained in the same manner as in Example 1 except that 10.2 g (0.11 mol) of aniline and 10.7 g (0.05 mol) of methane disulfonyl chloride were changed to 9.6 g (0.11 mol) of morpholine and 11.4 g (0.05 mol) of ethane disulfonyl chloride, respectively. The yield of ethane disulfonic acid bis-morpholine was 62.1% relative to ethane disulfonyl chloride.

Subsequently, 6.0 g (0.016 mol) of 1,2-difluoroethane disulfonic acid bis-morpholine (Compound 9) was obtained in the same manner as in Example 1 except that 9.8 g (0.03 mol) of methane disulfonic acid bis-phenylamide was changed to 9.9 g (0.03 mol) of ethane disulfonic acid bis-morpholine. The yield of 1,2-difluoroethane disulfonic acid bis-morpholine was 54.9% relative to ethane disulfonic acid bis-morpholine.

Preparation of Nonaqueous Electrolyte Solution

A nonaqueous electrolyte solution was prepared in the same manner as in the "Preparation of Nonaqueous Electrolyte Solution" of Example 1 except that Compound 9 was used in place of Compound 1 and the content thereof was set to 1.0% by mass.

Example 11

Preparation of 1,1,2,2-Tetrafluoroethane Disulfonic Acid Bis-Morpholine (Compound 10)

10.6 g (0.032 mol) of ethane disulfonic acid bis-morpholine (Compound 19) was obtained in the same manner as in Example 1 except that 10.2 g (0.11 mol) of aniline and 10.7 g (0.05 mol) of methane disulfonyl dichloride were changed to 9.6 g (0.11 mol) of morpholine and 11.4 g (0.05 mol) of ethane disulfonyl chloride, respectively. The yield of ethane disulfonic acid bis-morpholine was 64.6% relative to ethane disulfonyl chloride.

Subsequently, 6.9 g of (0.017 mol) of 1,1,2,2-tetrafluoroethane disulfonic acid bis-morpholine (Compound 10) was obtained in the same manner as in Example 1 except that 9.8 g (0.03 mol) of methane disulfonic acid bis-phenylamide was changed to 9.9 g (0.03 mol) of ethane disulfonic acid bis-morpholine and the amount of N-fluoro-N'-(chloromethyl)triethylenediamine bis-(tetrafluoroborate) was changed from 23.4 g (0.07 mol) to 46.8 g (0.13 mol). The yield of 1,1,2,2-tetrafluoroethane disulfonic acid bis-morpholine was 57.4% relative to ethane disulfonic acid bis-morpholine.

Preparation of Nonaqueous Electrolyte Solution

A nonaqueous electrolyte solution was prepared in the same manner as in the "Preparation of Nonaqueous Electrolyte Solution" of Example 1 except that Compound 10 was used in place of Compound 1 and the content thereof was set to 1.0% by mass.

Comparative Example 1

A nonaqueous electrolyte solution was prepared in the same manner as in Example 1 except that Compound 1 was not added in the "Preparation of Nonaqueous Electrolyte Solution".

Comparative Example 2

Methane disulfonic acid bis-phenylamide (Compound 11) was obtained in the same manner as in Example 1.

A nonaqueous electrolyte solution was prepared in the same manner as in Example 1 except that methane disulfonic acid bis-phenylamide (Compound 11) was used in place of Compound 1 and the content thereof was set to 1.0% by mass in the "Preparation of Nonaqueous Electrolyte Solution".

Comparative Example 3

Methane disulfonic acid bis-methylphenylamide (Compound 12) was obtained in the same manner as in Example 3.

A nonaqueous electrolyte solution was prepared in the same manner as in Example 1 except that methane disulfonic acid bis-methylphenylamide (Compound 12) was used in place of Compound 1 and the content thereof was set to 1.0% by mass in the "Preparation of Nonaqueous Electrolyte Solution".

Comparative Example 4

Methane disulfonic acid bis-methylbenzylamide (Compound 13) was obtained in the same manner as in Example 4.

A nonaqueous electrolyte solution was prepared in the same manner as in Example 1 except that methane disulfonic acid bis-methylbenzylamide (Compound 13) was used in place of Compound 1 and the content thereof was set to 1.0% by mass in the "Preparation of Nonaqueous Electrolyte Solution".

Comparative Example 5

Methane disulfonic acid bis-dibenzylamide (Compound 14) was obtained in the same manner as in Example 5.

A nonaqueous electrolyte solution was prepared in the same manner as in Example 1 except that methane disulfonic acid bis-dibenzylamide (Compound 14) was used in place of Compound 1 and the content thereof was set to 1.0% by mass in the "Preparation of Nonaqueous Electrolyte Solution".

Comparative Example 6

Methane disulfonic acid bis-(4-fluorophenylamide) (Compound 15) was obtained in the same manner as in Example 6.

A nonaqueous electrolyte solution was prepared in the same manner as in Example 1 except that methane disulfonic acid bis-(4-fluorophenylamide) (Compound 15) was used in place of Compound 1 and the content thereof was set to 1.0% by mass in the "Preparation of Nonaqueous Electrolyte Solution".

Comparative Example 7

Methane disulfonic acid bis-morpholine (Compound 16) was obtained in the same manner as in Example 7.

A nonaqueous electrolyte solution was prepared in the same manner as in Example 1 except that methane disulfonic acid bis-morpholine (Compound 16) was used in place of Compound 1 and the content thereof was set to 1.0% by mass in the "Preparation of Nonaqueous Electrolyte Solution".

Comparative Example 8

Methane disulfonic acid bis-piperidine (Compound 17) was obtained in the same manner as in Example 8.

A nonaqueous electrolyte solution was prepared in the same manner as in Example 1 except that methane disulfonic acid bis-piperidine (Compound 17) was used in place of Compound 1 and the content thereof was set to 1.0% by mass in the "Preparation of Nonaqueous Electrolyte Solution".

Comparative Example 9

Methane disulfonic acid bis-pyrrolidine (Compound 18) was obtained in the same manner as in Example 9.

A nonaqueous electrolyte solution was prepared in the same manner as in Example 1 except that methane disulfonic acid bis-pyrrolidine (Compound 18) was used in place of Compound 1 and the content thereof was set to 1.0% by mass in the "Preparation of Nonaqueous Electrolyte Solution".

Comparative Example 10

Ethanedisulfonic acid bis-morpholine (Compound 19) was obtained in the same manner as the method described in Example 10.

A nonaqueous electrolyte solution was prepared in the same manner as in Example 1 except that ethane disulfonic acid bis-morpholine (Compound 19) was used in place of Compound 1 and the content thereof was set to 1.0% by mass in the "Preparation of Nonaqueous Electrolyte Solution".

Comparative Example 11

1,3-Propanesultone (PS) (Compound 20) manufactured by Tokyo Chemical Industry Co., Ltd. was prepared.

A nonaqueous electrolyte solution was prepared in the same manner as in Example 1 except that 1,3-propanesultone (PS) (Compound 20) was used in place of Compound 1 and the content thereof was set to 1.0% by mass in the "Preparation of Nonaqueous Electrolyte Solution".

Comparative Example 12

Vinylene carbonate (VC) (Compound 21) manufactured by Tokyo Chemical Industry Co., Ltd. was prepared.

A nonaqueous electrolyte solution was prepared in the same manner as in Example 1 except that vinylene carbonate (VC) (Compound 21) was used in place of Compound 1 and the content thereof was set to 1.0% by mass in the "Preparation of Nonaqueous Electrolyte Solution".

Comparative Example 13

As fluoroethylene carbonate (FEC) (Compound 22), a product of Tokyo Chemical Industry Co., Ltd. was used.

A nonaqueous electrolyte solution was prepared in the same manner as in Example 1 except that fluoroethylene carbonate (FEC) (Compound 22) was used in place of Compound 1 and the content thereof was set to 1.0% by mass in the "Preparation of Nonaqueous Electrolyte Solution".

Evaluation

Compounds 1 to 22 obtained in Examples and Comparative Examples, and nonaqueous electrolyte solutions containing these compounds were evaluated as follows.

LUMO Energy

The lowest unoccupied molecular orbital (LUMO) energy of each of Compounds 1 to 10 used in Examples and Compounds 11 to 22 used in Comparative Examples was obtained by semi-empirical molecular orbital calculation, using a Gaussian 03 software. The LUMO energy of each of Compounds 1 to 22 obtained by orbital calculation is shown in Table 1.

TABLE 1

| Compound | Structure | LUMO Energy (eV) |
|---|---|---|
| 1 | (structure) | −0.77 |
| 2 | (structure) | −0.75 |
| 3 | (structure) | −0.81 |

TABLE 1-continued

| Compound | Structure | LUMO Energy (eV) |
|---|---|---|
| 4 | (dibenzylamino-SO2-CF2-SO2-dibenzylamino) | −0.74 |
| 5 | (4-F-C6H4-NH-SO2-CF2-SO2-NH-C6H4-4-F) | −0.88 |
| 6 | (morpholino-SO2-CF2-SO2-morpholino) | −0.01 |
| 7 | (piperidino-SO2-CF2-SO2-piperidino) | 0.04 |
| 8 | (pyrrolidino-SO2-CF2-SO2-pyrrolidino) | 0.05 |
| 9 | (morpholino-SO2-CHF-CHF-SO2-morpholino) | 0.07 |
| 10 | (morpholino-SO2-CF2-CF2-SO2-morpholino) | 0.02 |
| 11 | (PhNH-SO2-CH2-SO2-NHPh) | −0.62 |
| 12 | (PhN(CH3)-SO2-CH2-SO2-N(CH3)Ph) | −0.63 |
| 13 | (BnN(CH3)-SO2-CH2-SO2-N(CH3)Bn) | −0.45 |

TABLE 1-continued

| Compound | Structure | LUMO Energy (eV) |
|---|---|---|
| 14 | (dibenzylamino-SO2-CH2-SO2-dibenzylamino) | −0.65 |
| 15 | (4-F-C6H4-NH-SO2-CH2-SO2-NH-C6H4-4-F) | −0.71 |
| 16 | (morpholino-SO2-CH2-SO2-morpholino) | 0.19 |
| 17 | (piperidino-SO2-CH2-SO2-piperidino) | 0.27 |
| 18 | (pyrrolidino-SO2-CH2-SO2-pyrrolidino) | 0.29 |
| 19 | (morpholino-SO2-CH2-CH2-SO2-morpholino) | 0.36 |
| 20 | (1,3-propane sultone) | 1.13 |
| 21 | (vinylene carbonate) | 1.24 |
| 22 | (fluoroethylene carbonate) | 1.01 |

From Table 1, the LUMO energy of each of disulfonic acid amide compounds represented by Formula (1) (Compounds 1 to 10) is −0.88 eV to 0.07 eV, which was a generally low value as compared with the value of −0.71 eV to 0.36 eV of each of disulfonic acid amide compounds (Compounds 11 to 19) having no fluorine atom used in Comparative Examples.

The LUMO energy of each of the disulfonic acid amide compounds represented by Formula (1) and typified by Compounds 1 to 10 is lower than about 1.0 to about 2.0 eV, which is the LUMO energy of a common solvent used in a nonaqueous electrolyte solution (for example, LUMO energy of a cyclic carbonate or a chained carbonate is about 1.2 eV). Therefore, in a case where a nonaqueous electrolyte solution containing a disulfonic acid amide compound represented by Formula (1) as an additive is used in an electricity storage device such as a nonaqueous electrolyte solution secondary battery, electrochemical reduction of Compounds 1 to 10 occurs earlier than a solvent in the nonaqueous electrolyte solution, thereby forming a SEI on an electrode. Thus, decomposition of solvent molecules in the electrolyte solution can be suppressed. As a result, a film resulting from decomposition of the solvent which exhibits a high resistance is less likely to be formed on the electrode, and battery characteristics are improved.

Evaluation of Stability

For Compounds 1 to 10 used in Examples and Compounds 20 to 22 used in Comparative Examples, which were in a state of crystals before being added to a nonaqueous electrolyte solution, a storage test was performed for 90 days under constant temperature/constant humidity environments of a temperature of 40±2° C. and a humidity of 75±5%. Each compound before and after the storage was analyzed by high performance liquid chromatograph (HPLC) to obtain chromatograms. In the obtained chromatograms, a peak area ratio of each compound was considered as its purity, and from the purity change thereof before and after the storage test (difference in purity before and after the storage test), the stability of each compound after the storage test was evaluated. Small purity change means that a decomposition rate of the compound is small. The stability of each compound was evaluated in accordance with the following criteria. The results are shown in Table 2.

A: Less than 2.0% of purity change before and after the storage test

B: Greater than or equal to 2.0% and less than 5.0% of purity change before and after the storage test C: Greater than or equal to 5.0% of purity change before and after the storage test

TABLE 2

| | | Peak area ratio (Area %) | | |
|---|---|---|---|---|
| | Additive | Before storage test | After storage test | Stability |
| Examples 1 and 2 | Compound 1 | 99.3 | 98.6 | A |
| Example 3 | Compound 2 | 99.5 | 98.9 | A |
| Example 4 | Compound 3 | 99.5 | 98.6 | A |
| Example 5 | Compound 4 | 99.3 | 98.2 | A |
| Example 6 | Compound 5 | 99.7 | 99.4 | A |
| Example 7 | Compound 6 | 99.2 | 99.1 | A |
| Example 8 | Compound 7 | 99.6 | 98.4 | A |
| Example 9 | Compound 8 | 99.4 | 98.3 | A |
| Example 10 | Compound 9 | 99.3 | 98.0 | A |
| Example 11 | Compound 10 | 99.5 | 97.8 | A |
| Comparative Example 11 | Compound 20 (PS) | 99.6 | 94.8 | B |
| Comparative Example 12 | Compound 21 (VC) | 99.4 | 84.6 | C |
| Comparative Example 13 | Compound 22 (FEC) | 99.6 | 87.3 | C |

As shown in Table 2, 1,3-propane sultone (PS), vinylene carbonate (VC), and fluoroethylene carbonate (FEC) used in the Comparative Examples were considered to be partially decomposed during the storage test and had deteriorated stability. On the other hand, Compounds 1 to 10 used in Examples showed almost no change and was stable against moisture and temperature changes.

Manufacture of Battery $LiMn_2O_4$ as a positive electrode active material and carbon black as an electrical conductivity-imparting agent were dry-mixed. The mixture was uniformly dispersed in N-methyl-2-pyrrolidone (NMP) in which polyvinylidene fluoride (PVDF) as a binder had been dissolved, thereby manufacturing a slurry. The obtained slurry was applied on an aluminum metal foil (square, thickness of 20 μm) which was to be a positive electrode collector. NMP was evaporated from the coating film to manufacture a positive electrode sheet. The ratio of the solid contents in the obtained positive electrode sheet was as follows: positive electrode active material:electrical conductivity-imparting agent: PVDF=80:10:10 in terms of mass.

A commercially available graphite-coated electrode sheet (manufactured by Hohsen Corporation, trade name: ELECTRODE SHEET NEGATIVE ELECTRODE MONOLAYER) was used as a negative electrode sheet.

In each of the nonaqueous electrolyte solutions obtained in Examples and Comparative Examples, a negative electrode sheet and a positive electrode sheet were laminated via a separator made of polyethylene to manufacture a cylindrical secondary battery.

Measurement of Discharge Capacity Retention and Internal Resistance Ratio

Each of the obtained cylindrical secondary batteries was subjected to a charge/discharge cycle test under the conditions of a charging rate of 0.3 C, a discharging rate of 0.3 C, a charge termination voltage of 4.2 V, and a discharge termination voltage of 2.5 V at 25° C. The discharge capacity retention (%) and the internal resistance ratio after 200 cycles are shown in Table 3.

The "discharge capacity retention (%)" after 200 cycles is a value calculated by dividing the discharge capacity (mAh) after a 200-cycle test by the discharge capacity (mAh) after a 10-cycle test and multiplying the resulting value by 100. The "internal resistance ratio" after 200 cycles is expressed as a relative value of the resistance after the 200-cycle test in a case where the resistance before the cycle test was taken as 1.

TABLE 3

| | Additive | Discharge capacity retention (%) | Internal resistance ratio |
|---|---|---|---|
| Example 1 | Compound 1 (0.5% by mass) | 93 | 1.17 |
| Example 2 | Compound 1 (1.0% by mass) | 95 | 1.12 |
| Example 3 | Compound 2 (1.0% by mass) | 94 | 1.07 |
| Example 4 | Compound 3 (1.0% by mass) | 96 | 1.08 |
| Example 5 | Compound 4 (1.0% by mass) | 94 | 1.11 |
| Example 6 | Compound 5 (1.0% by mass) | 95 | 1.05 |
| Example 7 | Compound 6 (1.0% by mass) | 95 | 1.06 |
| Example 8 | Compound 7 (1.0% by mass) | 94 | 1.10 |
| Example 9 | Compound 8 (1.0% by mass) | 96 | 1.15 |
| Example 10 | Compound 9 (1.0% by mass) | 97 | 1.11 |

TABLE 3-continued

| | Additive | Discharge capacity retention (%) | Internal resistance ratio |
|---|---|---|---|
| Example 11 | Compound 10 (1.0% by mass) | 96 | 1.08 |
| Comparative Example 1 | No additive | 74 | 1.83 |
| Comparative Example 2 | Compound 11 (1.0% by mass) | 90 | 1.29 |
| Comparative Example 3 | Compound 12 (1.0% by mass) | 91 | 1.24 |
| Comparative Example 4 | Compound 13 (1.0% by mass) | 92 | 1.34 |
| Comparative Example 5 | Compound 14 (1.0% by mass) | 91 | 1.31 |
| Comparative Example 6 | Compound 15 (1.0% by mass) | 89 | 1.25 |
| Comparative Example 7 | Compound 16 (1.0% by mass) | 92 | 1.27 |
| Comparative Example 8 | Compound 17 (1.0% by mass) | 92 | 1.33 |
| Comparative Example 9 | Compound 18 (1.0% by mass) | 91 | 1.26 |
| Comparative Example 10 | Compound 19 (1.0% by mass) | 92 | 1.24 |
| Comparative Example 11 | Compound 20 (PS) (1.0% by mass) | 81 | 1.68 |
| Comparative Example 12 | Compound 21 (VC) (1.0% by mass) | 81 | 1.69 |
| Comparative Example 13 | Compound 22 (FEC) (1.0% by mass) | 84 | 1.66 |

As shown in Table 3, it can be seen that the cylindrical secondary batteries using the nonaqueous electrolyte solutions of Examples 1 to 11 containing Compounds 1 to 10 as an additive for nonaqueous electrolyte solutions exhibit high discharge capacity retention in the cycle test, as compared with the cylindrical secondary batteries using the nonaqueous electrolyte solutions of Comparative Example 1 and Comparative Examples 11 to 13. Furthermore, it can be seen that the cylindrical secondary batteries using the nonaqueous electrolyte solutions of Examples 1 to 11 exhibit high discharge capacity retention in the cycle test, even as compared with those using the nonaqueous electrolyte solutions which contain disulfonic acid amide compounds of Compounds 11 to 19 having no fluorine atom. From these results, it can be seen that in a case where the nonaqueous electrolyte solutions containing Compounds 1 to 10 of Examples as an additive for nonaqueous electrolyte solutions are used in a nonaqueous electrolyte solution secondary battery or the like, a SEI which is highly stable for charge/discharge cycles is formed on the surface of an electrode of the nonaqueous electrolyte solution secondary battery or the like, as compared with commonly used nonaqueous electrolyte solutions containing a cyclic carbonate, a chained carbonate, or the like. In addition, it can be seen that since the internal resistance ratio of Examples 1 to 11 is low, Compounds 1 to 10 can suppress an increase in internal resistance due to the cycle test.

Gas Generation Test

In addition to the batteries used in the cycle test, a nonaqueous electrolyte solution secondary battery having the same constitution which includes each of the nonaqueous electrolyte solutions of Examples and Comparative Examples was prepared. An operation in which the battery was charged to 4.2 V at a current corresponding to 0.2 C, and then discharged to 3 V at a current corresponding to 0.2 C, were repeated in two cycles at 25° C. to stabilize the battery.

Subsequently, the battery was charged again to 4.2 V at a charging rate of 0.3 C, and then allowed to stand under the environment of 60° C. for 168 hours. Thereafter, the battery was cooled to room temperature. The amount of gas generated from the battery after being left to stand was measured by the Archimedes' method. The results are shown in Table 4.

TABLE 4

| | Additive | Amount of Gas Generated (ml) |
|---|---|---|
| Example 1 | Compound 1 0.5% by mass | 0.78 |
| Example 2 | Compound 1 1.0% by mass | 0.59 |
| Example 3 | Compound 2 1.0% by mass | 0.55 |
| Example 4 | Compound 3 1.0% by mass | 0.61 |
| Example 5 | Compound 4 1.0% by mass | 0.46 |
| Example 6 | Compound 5 1.0% by mass | 0.49 |
| Example 7 | Compound 6 1.0% by mass | 0.54 |
| Example 8 | Compound 7 1.0% by mass | 0.65 |
| Example 9 | Compound 8 1.0% by mass | 0.72 |
| Example 10 | Compound 9 1.0% by mass | 0.46 |
| Example 11 | Compound 10 1.0% by mass | 0.44 |
| Comparative Example 1 | No additive | 1.50 |
| Comparative Example 2 | Compound 11 1.0% by mass | 0.98 |
| Comparative Example 3 | Compound 12 1.0% by mass | 1.05 |
| Comparative Example 4 | Compound 13 1.0% by mass | 1.02 |
| Comparative Example 5 | Compound 14 1.0% by mass | 0.99 |
| Comparative Example 6 | Compound 15 1.0% by mass | 0.94 |
| Comparative Example 7 | Compound 16 1.0% by mass | 0.88 |
| Comparative Example 8 | Compound 17 1.0% by mass | 1.05 |
| Comparative Example 9 | Compound 18 1.0% by mass | 1.06 |
| Comparative Example 10 | Compound 19 1.0% by mass | 0.91 |
| Comparative Example 11 | Compound 20 (PS) 1.0% by mass | 1.25 |
| Comparative Example 12 | Compound 21 (VC) 1.0% by mass | 1.64 |
| Comparative Example 13 | Compound 22 (FEC) 1.0% by mass | 1.69 |

As shown in the results of Table 4, it can be seen that disulfonic acid amides (Compounds 1 to 10) represented by Formula (1) are excellent in gas generation-suppressing effect, as compared with compounds of Comparative Examples (Compounds 11 to 19).

As shown in the results of Tables 1 to 4, it can be seen that Compounds 1 to 10 have excellent storage stability and can form a stable SEI on the surface of an electrode to improve battery characteristics in terms of cycle characteristics and gas generation in a case of being used in an electricity storage device such as a nonaqueous electrolyte solution secondary battery.

INDUSTRIAL APPLICABILITY

The invention can provide an additive for nonaqueous electrolyte solutions capable of improving battery characteristics such as lifetime and capacity. In addition, according to the invention, it is possible to provide a nonaqueous electrolyte solution using the additive for nonaqueous electrolyte solutions, and an electricity storage device using the nonaqueous electrolyte solution.

REFERENCE SIGNS LIST

1: Nonaqueous electrolyte solution secondary battery,
2: Positive electrode collector,
3: Positive electrode active material layer,
4: Positive electrode plate,
5: Negative electrode collector,
6: Negative electrode active material layer,
7: Negative electrode plate,
8: Nonaqueous electrolyte solution,
9: Separator.

The invention claimed is:
1. An additive for nonaqueous electrolyte solutions, comprising a disulfonic acid amide compound represented by Formula (1),

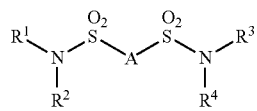

(1)

in Formula (1),
A represents a $C_mH_{(2m-n)}Z_n$, wherein m represents an integer of 1 to 6, n represents an integer of 1 to 12, 2m-n is 0 or more, and Z represents a halogen atom,
$R^1$ represents a phenyl group optionally having a substituent, a phenylthio group optionally having a substituent, a phenoxy group optionally having a substituent, a phenylamino group optionally having a substituent, or an alkyl group having 1 to 6 carbon atoms which is substituted with a phenyl group optionally having a substituent, wherein a sulfur atom, an oxygen atom, or an amino group optionally having a substituent may intervene between two carbon atoms of the alkyl group, between one carbon atom of the alkyl group and the phenyl group optionally having a substituent, or between one carbon atom of the alkyl group and a nitrogen atom to which $R^1$ is bonded,
$R^2$, $R^3$, and $R^4$ each independently represent a hydrogen atom, a phenyl group optionally having a substituent, a phenylthio group optionally having a substituent, a phenoxy group optionally having a substituent, a phenylamino group optionally having a substituent, or an alkyl group having 1 to 6 carbon atoms which may be substituted with a phenyl group optionally having a substituent, wherein a sulfur atom, an oxygen atom, or an amino group optionally having a substituent may intervene between two carbon atoms of the alkyl group, between one carbon atom of the alkyl group and the phenyl group optionally having a substituent, or between one carbon atom of the alkyl group and a nitrogen atom to which $R^2$, $R^3$, or $R^4$ is bonded,
$R^1$ and $R^2$ may be linked to form an alkylene group having 2 to 5 carbon atoms in total which forms a cyclic structure together with a nitrogen atom to which they are bonded, wherein a sulfur atom, an oxygen atom, or an amino group optionally having a substituent may intervene between two carbon atoms of the alkylene group, or between one carbon atom of the alkylene group and the nitrogen atom to which $R^1$ and $R^2$ are bonded,
$R^3$ and $R^4$ may be linked to form an alkylene group having 2 to 5 carbon atoms in total which forms a cyclic structure together with a nitrogen atom to which they are bonded, wherein a sulfur atom, an oxygen atom, or an amino group optionally having a substituent may intervene between two carbon atoms of the alkylene group, or between one carbon atom of the alkylene group and the nitrogen atom to which $R^3$ and $R^4$ are bonded.

2. The additive for nonaqueous electrolyte solutions according to claim 1,
wherein Z in Formula (1) is a fluorine atom.

3. The additive for nonaqueous electrolyte solutions according to claim 1,
wherein in Formula (1), $R^3$ and $R^1$ are the same group, and $R^2$ and $R^4$ are the same group.

4. The additive for nonaqueous electrolyte solutions according to claim 1,
wherein in Formula (1),
$R^1$ and $R^2$ are linked to form an alkylene group having 2 to 5 carbon atoms in total which forms a cyclic structure together with a nitrogen atom to which they are bonded, wherein a sulfur atom, an oxygen atom, or an amino group optionally having a substituent may intervene between two carbon atoms of the alkylene group, or between one carbon atom of the alkylene group and the nitrogen atom to which $R^1$ and $R^2$ are bonded, and
$R^3$ and $R^4$ are linked to form an alkylene group having 2 to 5 carbon atoms in total which forms a cyclic structure together with a nitrogen atom to which they are bonded, wherein a sulfur atom, an oxygen atom, or an amino group optionally having a substituent may intervene between two carbon atoms of the alkylene group, or between one carbon atom of the alkylene group and the nitrogen atom to which $R^1$ and $R^2$ are bonded.

5. A nonaqueous electrolyte solution comprising:
the additive for nonaqueous electrolyte solutions according to claim 1;
a nonaqueous solvent; and
an electrolyte.

6. The nonaqueous electrolyte solution according to claim 5,
wherein the nonaqueous solvent comprises an aprotic solvent.

7. The nonaqueous electrolyte solution according to claim 6,
wherein the aprotic solvent is at least one selected from the group consisting of a cyclic carbonate, a chained carbonate, an aliphatic carboxylic acid ester, a lactone, a lactam, a cyclic ether, a chained ether, a sulfone, and a halogen derivative thereof.

8. The nonaqueous electrolyte solution according to claim 5,
wherein the electrolyte comprises a lithium salt.

9. The nonaqueous electrolyte solution according to claim 8,
wherein the lithium salt is at least one selected from the group consisting of $LiAlCl_4$, $LiBF_4$, $LiPF_6$, $LiClO_4$, $LiAsF_6$, and $LiSbF_6$.

10. An electricity storage device comprising:
the nonaqueous electrolyte solution according to claim 5;
a positive electrode; and
a negative electrode.

11. The electricity storage device according to claim 10, wherein the electricity storage device is a lithium ion battery.

12. The electricity storage device according to claim 10, wherein the electricity storage device is a lithium ion capacitor.

* * * * *